United States Patent [19]

Gartner

[11] Patent Number: 5,627,135
[45] Date of Patent: May 6, 1997

[54] SUSPENSION FOMULATIONS OF 2,2-DIBROMO-3-NITRILOPROPIONAMIDE

[75] Inventor: Charles D. Gartner, Midland, Mich.

[73] Assignee: The Dow Chemical Company, Midland, Mich.

[21] Appl. No.: 618,908

[22] Filed: Mar. 20, 1996

[51] Int. Cl.$^6$ .......................... A01N 25/04; A01N 37/18; A01N 37/34
[52] U.S. Cl. .......................... 504/159; 514/528; 514/777; 514/780; 514/937; 514/949
[58] Field of Search .......................... 504/159; 514/528, 514/937, 949, 777, 780

[56] References Cited

U.S. PATENT DOCUMENTS

| | | | |
|---|---|---|---|
| 3,948,636 | 4/1976 | Marks | 71/112 |
| 3,996,378 | 12/1976 | Payton | 424/302 |
| 4,241,080 | 12/1980 | Burk | 424/304 |
| 4,770,694 | 9/1988 | Iwasaki et al. | 71/93 |
| 4,800,082 | 1/1989 | Karbowski et al. | 424/409 |
| 4,963,586 | 10/1990 | Katayama et al. | 514/547 |

FOREIGN PATENT DOCUMENTS

| | | |
|---|---|---|
| 0281460 | 2/1987 | European Pat. Off. . |
| 2309983 | 1/1972 | Germany . |
| 132400 | 9/1980 | Japan . |
| 333349 | 12/1987 | Japan . |
| WO9500019 | 1/1995 | WIPO . |

OTHER PUBLICATIONS

Nagui I. Ibrahim and Dev K. Mehra, "Colloidal Microcrystalline Cellulose as a Thickener in Flowables," *Pesticide Formulations and Applications Systems*, vol. 12, Issue 1146, 1993, pp. 116–132.

*Primary Examiner*—S. Mark Clardy
*Attorney, Agent, or Firm*—Gregory L. Porter; James M. Pelton; Stephen S. Grace

[57] ABSTRACT

Stable, concentrated aqueous suspensions of 2,2-dibromo-3-nitrilopropionamide which contribute minimal chemical oxygen demand to systems treated therewith and methods of preparing and using said suspensions in biocidal applications have been discovered. The formulations comprise from about 3 to about 70 weight percent 2,2-dibromo-3-nitrilopropionamide suspended in about 30 to about 97 weight percent water in the presence of a suspending amount of a thixotrope that exhibits Ellis-Plastic behavior, such as xantham gum and locust bean gum, at a pH of from about 1 to about 4.

13 Claims, No Drawings

SUSPENSION FOMULATIONS OF 2,2-DIBROMO-3-NITRILOPROPIONAMIDE

FIELD OF THE INVENTION

The present invention concerns stable, concentrated aqueous suspensions of 2,2-dibromo-3-nitrilopropionamide and methods of preparing and using said suspensions in biocidal applications.

BACKGROUND OF THE INVENTION 2,2-Dibromo-3-nitrilopropionamide (DBNPA) is a well-known compound useful in aqueous systems due to its biocidal activity. DBNPA has proven especially useful in controlling the fouling of cooling towers due to slime accumulation and in removing slime from wood pulp prior to processing operations in the paper industry. See, for example, U.S. Pat. Nos. 3,751,444; 4,163,796;, 4,241,080; and 4,328,171.

For many antimicrobial applications, it is desirable to employ DBNPA in a liquid concentrate composition for ease of shipment, storage, and especially for dispersibility in aqueous systems. Due to its cost, availability, and safety, water would be an ideal solvent for use in preparing such concentrates. Unfortunately, since DBNPA is only slightly soluble in water and usually degrades after prolonged contact with water, its use in such concentrates has not been found to be acceptable. See for example, "Rates and Products of Decomposition of 2,2-dibromo-3-nitrilopropionamide", Exner et al., *J. Agr. Food Chem.*, Vol. 21, No. 5, pp. 838–842.

Because water has an adverse impact upon DBNPA, various types of stabilizers and non-aqueous solvents have been utilized in preparing liquid formulations of DBNPA. A recent commercial group of stabilizers for DBNPA are the polyalkylene glycols as disclosed in U.S. Pat. No. 5,070,105.

Unfortunately, commercial formulations comprising DBNPA, a polyalkylene glycol such as tetraethylene glycol, and water are fairly expensive due to the cost of the polyalkylene glycol. In addition, the DBNPA still degrades significantly over the course of time. Yet another disadvantage of this formulation includes the environmental concerns associated with employing polyalkylene glycols.

One such environmental concern is that increased chemical oxygen demand of the industrial waste water, e.g., cooling tower effluent, results when DBNPA is employed with organic solvents such as polyalkylene glycols. Chemical oxygen demand represents the amount of oxygen consumed in the oxidation of organic and oxidizable inorganic material contained in the waste water. See Richard J. Lewis, *Hawley's Condensed Chemical Dictionary*, Twelfth Edition, 1993, p. 253. A high chemical oxygen demand is undesirable for a body of water whether the body be a wastewater treatment pool or a natural body of water.

A high chemical oxygen demand for a body of water is undesirable because biodegradation of microorganisms may cause oxygen depletion in said body of water. If the body of water is a wastewater treatment pool then oxygen depletion could be detrimental to the efficient operation of the wastewater treatment plant. If the body of water is a natural body of water then oxygen depletion could be detrimental to aquatic life which require oxygen for survival.

Formulations comprised of DBNPA and organic solvents contribute more chemical oxygen demand than if DBNPA is employed alone or with non-organic solvents because organic solvents serve as a feeding ground for microorganisms by providing nutrients. Therefore, even though the DBNPA may destroy a majority of the microorganisms before it degrades, a few microorganisms still survive. Those few microoganisms multiply very rapidly in the presence of an organic solvent. Therefore, when DBNPA-treated waste water containing an organic solvent is released to the environment, or even if it is in a closed system, chemical oxygen demand will increase significantly over time due to the rapidly multiplying microorganisms consuming oxygen in the water.

It would be desirable to discover liquid formulations of DBNPA that utilize water as a suspending medium and in which the DBNPA is protected to prevent or reduce the decomposition or degradation thereof. This type of formulation would not only reduce the chemical oxygen demand as compared to the present commercial formulations which employ polyalkylene glycols, but such a formulation would also be less expensive. It would also be advantageous if a wide range of concentrations of DBNPA could be employed in the formulations. Furthermore, it would be desirable if the formulations were insensitive to changes in temperature and electrolyte concentration.

SUMMARY OF THE INVENTION

Surprisingly, it has been discovered that novel formulations of DBNPA can be produced which have a lower chemical oxygen demand than previous formulations. Even more surprisingly, the novel, less expensive formulations employ water as a suspending medium and less degradation of DBNPA results than when known organic solvents are employed. A wide range of concentrations of DBNPA are useful, i.e., about three weight percent to about 70 weight percent DBNPA are possible in formulations of the invention. The formulations are substantially insensitive to changes in temperature from about 0° to about 100° C. and to changes in the electrolyte concentration.

The formulation comprises a suspension of DBNPA and water in the presence of a suspending amount of a thixotrope which exhibits Ellis-Plastic behavior over a pH range of from about 1 to about 4. These thixotropes include such natural gums as xantham gum and locust bean gum, such clays as bentonites, and mixtures thereof.

The present invention also includes a process of making the above formulations as well as a method of using the above formulations. The process comprises suspending from at least about 3, preferably at least about 20, more preferably at least about 50, to at most about 70 weight percent DBNPA in at least about 30, preferably at least about 40, to at most about 97 weight percent water in the presence of a suspending amount of a thixotrope which exhibits Ellis-Plastic behavior over a pH range of from about 1 to about 4. The above formulations are useful as a method for biological control in an aqueous industrial system in need of such control which comprises contacting the system with an antimicrobially effective amount of the above formulation.

The term "thixotrope exhibiting Ellis-Plastic behavior" refers to compounds or mixtures of compounds which cause a formulation to exhibit the following properties. First, the formulation must form a gel which liquefies when agitated, yet returns to the gel state when it is at rest. Second, in contrast to most liquids which will flow when subjected to any shear stress, i.e., force applied to the liquid, no matter how small the stress, formulations of this invention require some minimum amount of shear stress in order to liquefy the formulation and cause it to flow. This minimum amount of shear stress is called the "yield value" and it varies as the particular thixotrope and its concentration vary. The yield value of the thixotrope must be high enough to suspend DBNPA particles in water. This means the yield value must exceed the force of gravity acting on the DBNPA particles or the DBNPA will settle to the bottom. In general, the minimum yield value necessary to suspend a spherical particle may be determined by the following equation: minimum yield value $=(4/3)(C_r)(\rho_p-\rho_m)$ wherein $C_r$ represents the radius of the particles to be suspended, $\rho_p$ represents the density of the particles to be suspended, and $\rho_m$ represents the density of the suspending matrix. See, for example, Carbopol™ Bulletin DET-3 from BF Goodrich 3/93. Thus, the yield value will necessarily be higher when larger DBNPA particles are employed in the formulation. Thirdly, the thixotrope must cause the formulation to exhibit "shear thinning" behavior. This means that when the shear stress is above the yield value, the viscosity of the formulation will be reduced as the shear stress increases. The thixotrope must exhibit these properties over a pH range of from about 1 to about 4 to be effective in a formulation with DBNPA because when DBNPA is added to water, the pH normally equilibrates this level.

The term "suspending amount" refers to that amount of thixotrope that provides for suspending DBNPA particles such that less than about 5, preferably less than about 3, percent of the DBNPA settles to the bottom during conventional shipment and storage for about 6–12 months, yet still allows the suspension to be pumped as a liquid upon slight agitation.

The term "antimicrobial" refers to the function of DBNPA as a biocide, i.e., inhibits the growth of, or kills, microorganisms such as bacteria, molds, yeasts, algae, protozoa, etc.

The term "effective amount" refers to that amount of the antimicrobial formulation of the present invention which will provide for biological control in aqueous systems. The term "biological control" or "biologically controlling" refers to prevention, reduction, or elimination of any adverse consequences such as slime formation, corrosion, odor, etc., in aqueous industrial systems that are directly, indirectly, or otherwise due to the presence and/or growth of microorganisms.

The aqueous systems contemplated for application of the method of the present invention include those aqueous industrial systems susceptible to growth, accumulation, or presence of microorganisms; for example, cooling towers, pulp and paper mills, metalworking fluids, air washers, and the like.

DETAILED DESCRIPTION OF THE INVENTION

Suitable thixotropes for suspending DBNPA in water according to this invention include those which exhibit Ellis-Plastic behavior at a pH of from about 1 to about 4, preferably from a pH of about 2 to about 3. These thixotropes typically exhibit a yield value which exceeds the force of gravity acting on the DBNPA particles thereby allowing the DBNPA particles to be suspended in water and thus protected from the degrading effects water usually has upon DBNPA. Useful thixotropes include natural gums such as xantham gum and locust bean gum, clays such as bentonites and mixtures thereof. Other thixotropes useful in this invention may be determined by the following test.

Test for Determining Suitable Thixotropes

1. In a cylindrically shaped vessel, a uniform mixture of the thixotrope to be tested is prepared by admixing a predetermined amount of the thixotrope in a predetermined amount of water to give various predetermined concentrations of the thixotrope in water. A series of mixtures ranging from 0.1 weight percent to 2 weight percent thixotrope in water are thus prepared. To each of these mixtures, a predetermined amount of solid DBNPA is then added with agitation to prepare a series of formulations containing from 3 to 70 weight percent DBNPA. Typically, a few minutes of agitation is sufficient to achieve a uniform suspended mixture in the form of a gel for each formulation. However, three hours should pass before Step 2 is undertaken in order that the formulation reaches an equilibrium at which it will exhibit its final thixotropic properties.

2. After three hours have passed, the formulations can now be tested for suitability in the invention. Gentle agitation is applied to the formulations. If little or no flow occurs upon agitation of the formulation then the thixotrope is not suitable for use in the invention. Suitable thixotropes (assuming they exhibit suitable yield value and stability as determined in step three below) should cause the formulation to liquefy and flow upon agitation and return to its gel form almost immediately upon cessation of agitation.

3. The formulation's yield value and stability are tested by storing the suspended gel mixtures at about 40° C. for four weeks. If the formulation has not settled in this time then the thixotrope is suitable for use in the invention. Non-uniformity of the formulation indicates unsuitability of the thixotrope for use in this invention. Non-uniformity is detected by the formation of an appreciably particle free upper liquid layer and/or a dense solid bottom layer. If less than about 5 percent of the solid DBNPA has settled to the bottom or if less than about 10 volume percent of a substantially particle free upper layer has formed, the thixotrope is acceptable for use in formulations of this invention. The amount of solid DBNPA at the bottom, if any, can be determined by decanting the formulation to leave only the solid DBNPA that had settled. The solid DBNPA is then dried and weighed to determine if more than 5 percent of the total DBNPA has settled. If more than 5 percent of the DBNPA is present then the thixotrope is unacceptable. If a particle free upper liquid layer exists then it can be determined if said layer is more than 10 volume percent by dividing the depth of the upper layer by the depth of the total formulation. If the ratio is more than 0.1 (10 percent) then the thixotrope is unacceptable.

Once a thixotrope has been identified as useful in the invention by the above test, the suspending amount of thixotrope necessary must be determined. Typically, this amount will vary depending upon the nature of the thixotrope as well as the amount of DBNPA and water present. However, in general the amount of thixotrope should not be so much that the suspension becomes too thick to be pumped as a liquid. On the other hand, the amount should be sufficient to suspend and maintain the DBNPA in water with less than about 5, preferably less than about 3, percent of the DBNPA settling during conventional shipment and storage of the suspension for 6–12 months. Generally, the suspending amount is at least about 0.03 weight percent of the total suspension, preferably at least about 0.8, to at most about 4, preferably to at most about 2 weight percent of the total suspension. A preferred thixotrope and amount is a mixture of from about 0.05 to about 1.5 weight percent xantham gum and about 0.01 to about 0.5 weight percent locust bean gum.

Advantageously, formulations of this invention may be made which utilize a wide range of DBNPA concentrations. This allows the utilization of a concentration of DBNPA that is suitable for a particular application as well as a concentration that is convenient to ship and store. Although the concentration of which the formulation is capable may vary with the particular thixotrope chosen, it is usually from at least about 3, preferably at least about 5 weight percent DBNPA to at most about 70, preferably at most about 60 weight percent DBNPA. This is due to the fact that with most thixotropes, if more than about 70 weight percent DBNPA is employed then the formulation will exhibit a clay-like consistency and not readily disperse when employed in an aqueous system. On the other hand, since about 1.5 weight percent of DBNPA dissolves in water, it is not practical to employ less than about 3 percent.

Although it is not required, it is desirable to use the crystalline form of DBNPA for ease of dispersing and suspending it in the water. Smaller crystals are generally desirable. This is due to the fact that the required yield value of the thixotrope will be less, as described above, as well as the fact that the DBNPA will more rapidly disperse in the water. However, the DBNPA particles should not be so small that DBNPA dust is problematic. Generally, DBNPA particle sizes of about 160–180 microns×50–70 microns×50–70 microns are very effective when used with a thixotrope such as xantham gum, locust bean gum or such clays as bentonites or mixtures thereof.

Water comprises the remainder of the formulation and functions as the suspending medium in which the DBNPA is substantially uniformly dispersed. It is not necessary that the water be distilled or purified. Normal water, for example tap, well, or distilled, may be employed in most applications. Typically, water is employed in an amount of from at least about 30, preferably at least about 40, to at most about 97, preferably at most about 95 weight percent of the total formulation.

Although it is not necessary in most instances, it may be desirable to acidify the formulation before adding the DBNPA to the water if the pH of the water is initially above 7. This is due to the fact that DBNPA will degrade more rapidly and to a greater extent at higher pH's. In general, almost any acidifying agent may be used, for example oxalic acid, acetic acid, citric acid, carboxylic acids, and mineral acids such as phosphoric, sulfuric and hydrobromic may be usefully employed. The type of acid and amount may be varied based upon the particular thixotrope, amount of DBNPA, and the desired application. The amount that should be employed will be apparent to one skilled in the art in that the pH of the water should be reduced below about 7 before addition of the DBNPA. Upon addition of the DBNPA, the pH of the formulation will usually equilibrate to about 1 to about 4 and no further acidification is usually needed.

Although the ingredients of the formulation may be mixed together in any order, for ease of mixing it is desirable to slowly add the suspending amount of thixotrope to a known amount of tap water while agitating until the thixotrope is well dispersed. The DBNPA is then added with agitation. The temperature is conveniently about 25° C. although higher temperatures may cause the thixotrope and DBNPA to mix more rapidly with the water but the temperature should not be so high that the water boils.

The formulation of the present invention can optionally have other active or inert ingredients conventionally employed in such types of formulations such as corrosion inhibitors, scale inhibitors, colorants, fragrances, etc.

The formulations of the present invention are useful for many different applications. Among useful applications are controlling bacteria in cooling systems and controlling bacteria, fungi, and algae in recirculating water cooling towers and air washer systems. Although dosage rates vary by application, typical dosage rates are from about 0.5 to about 5 parts per million of active DBNPA with a higher initial dose than subsequent doses.

The present invention is illustrated by the following examples; however, the examples should not be interpreted as a limitation upon the scope of the present invention. All percentages are by weight of total formulation unless otherwise indicated.

EXAMPLE 1

A premeasured amount of a mixture of xanthan gum and locust bean gum was slowly added to well stirred tap water. Mixing was continued until the gum mixture was thoroughly dispersed in the solution. The solution was held at room temperature for thirty minutes. While mixing again, a predetermined amount of oxalic acid was then added followed by a predetermined amount of DBNPA. The percentage of each of the ingredients utilized, as well as the pH of the formulations, are exemplified in Table I.

Examples 2, 3, and 4 were prepared in substantially the same manner employing varying amounts of xanthan gum, locust bean gum, water, oxalic acid, and DBNPA as shown in Table I.

The xanthan gum employed was TICAXAN Xanthan Powder™ (available from TIC Gums) and the locust bean gum employed was Locust Bean POR/A TIC Powder™ (available from TIC Gums).

TABLE I

| | Xanthan | Locust Bean | Water | Oxalic Acid | DBNPA (1) | pH |
| --- | --- | --- | --- | --- | --- | --- |
| Example 1 | 1.000 | 0.335 | 48.67 | 0.030 | 49.97 | 2.4 |
| Example 2 | 0.772 | 0.259 | 48.94 | 0.023 | 50.01 | 2.4 |
| Example 3 | 0.516 | 0.173 | 49.45 | 0.015 | 49.85 | 2.4 |
| Example 4 | 0.305 | 0.102 | 49.62 | 0.009 | 49.96 | 2.4 |

(1) All values in weight percent except pH.

Stability tests involving aging studies and freeze-thaw cycles were conducted on the formulations of Examples 1–4.

The aging studies upon Examples 1–4 consisted of storing the suspensions at a temperature of about 22° C. for a period of 12 months. When measured by high pressure liquid chromatography, no measurable loss in the total DBNPA was detected for the formulations of Examples 1–4.

Freeze-thaw cycles consisted of subjecting the formulations of Examples 1–4 to a temperature of –29° C. for a period of 16 hours followed by 8 hours at room temperature with no agitation. No appreciable degradation of DBNPA occurred in Examples 1–4 and all remained suspended over the course of 23 days. By the 30th day the formulation of Example 4 had settled.

The chemical oxygen demand of the formulations of Examples 1–4 can be calculated to be about 1.08 parts per million (ppm) for every one ppm of DBNPA employed. This compares very favorably to commercial formulations which employ 20 percent DBNPA, 20 percent water, and 60 percent tetraethylene glycol and exhibit a calculated chemical oxygen demand of 5.85 ppm for every one ppm of DBNPA.

The stability of the formulations of Examples 1–4, at a constant temperature of 20° C. and pH of 3.0, can be calculated to chow that 99.82 percent DBNPA remains after 9 months. This compares very favorably to the stability of commercial formulations which employ 20 percent DBNPA, 20 percent water, and 60 percent tetraethylene glycol at a constant temperature of 20° C. and pH of 3.0 which exhibit a calculated amount of only 91.8 percent of the DBNPA remaining after 9 months.

The antimicrobial activity of the compounds of the present invention, illustrated by compound Example No. I and II of Table II, is demonstrated by the following techniques.

TABLE II

Identification of Compounds Used in
Antimicrobial Activity Tests

| Compound Example No. | Chemical Identity |
|---|---|
| I | Suspension of 50 weight percent DBNPA, 0.75 weight percent xanthan gum, 0.25 weight percent locust bean gum, and 49 weight percent water which suspension was freshly prepared before antimicrobial activity test |
| II | Suspension of 50 weight percent DBNPA, 0.75 weight percent xanthan gum, 0.25 weight percent locust bean gum, and 49 weight percent water which suspension was aged for over 15 months before antimicrobial activity test |

The minimum inhibitory concentration (MIC) for the compounds listed in Table II is determined for 9 bacteria, using nutrient agar, and 7 yeast and fungi, using malt yeast agar. A one percent solution of the test compound is prepared in a mixture of acetone and water.

Nutrient agar is prepared at pH 6.8, representing a neutral medium, and at pH 8.2, representing an alkaline medium. The nutrient agars are prepared by adding 23 g of nutrient agar to one liter of deionized water. In addition, the alkaline medium is prepared by adjusting a 0.04M solution of N-[tris-(hydroxymethyl)methyl]glycine buffered deionized water with concentrated sodium hydroxide to a pH of 8.5.

Malt yeast agar is prepared by adding 3 g yeast extract and 45 g malt agar per liter of deionized water. The specific agar is dispensed in 30 mL aliquots into 25×200 mm test tubes, capped and autoclaved for 15 minutes at 115° C.

The test tubes containing the agar are cooled in a water bath until the temperature of the agar is 48° C. Then, an appropriate amount of the one percent solution of the test compound is added (except in the controls where no compound is added) to the respective test tubes so that the final concentrations are 500, 250, 100, 50, 25, 10, 5, 2.5, 1.0 and zero parts per million of the test compound in the agar, thus having a known concentration of test compound dispersed therein. The contents of the test tubes are then transferred to respective petri plates. After drying for 24 hours, the petri plates containing nutrient agar are inoculated with bacteria and those containing malt yeast agar are inoculated with yeast and fungi.

The inoculation with bacteria is accomplished by using the following procedure. Twenty-four hour cultures of each of the bacteria are prepared by incubating the respective bacteria in tubes containing nutrient broth for 24 hours at 30° C. in a shaker. Dilutions of each of the 24 hour-cultures are made so that nine separate suspensions (one for each of the nine test bacteria) are made, each containing 108 colony forming units (CFU) per mL of suspension of a particular bacteria. Aliquots of 0.3 mL of each of the bacterial suspensions are used to fill the individual wells of Steer's Replicator. For each microbial suspension, 0.3 mL was used to fill three wells (that is, three wells of 0.3 mL each) so that for the nine different bacteria, 27 wells are filled. The Steer's Replicator is then used to inoculate both the neutral and alkaline pH nutrient agar petri plates.

The inoculated petri plates are incubated at 30° C. for 48 hours and then read to determine if the test compound which is incorporated into the agar prevented growth of the respective bacteria.

The inoculation with the yeast and fungi is accomplished as follows. Cultures of yeast and fungi are incubated for seven days on malt yeast agar at 30° C. These cultures are used to prepare suspensions by the following procedure. A suspension of each organism is prepared by adding 10 mL of sterile saline and 10 microliters of octylphenoxy polyethoxy ethanol to the agar slant of yeast or fungi. The sterile saline/octylphenoxy polyethoxy ethanol solution is then agitated with a sterile swab to suspend the microorganism grown on the slant. Each resulting suspension is diluted into sterile saline (1 part suspension to 9 parts sterile saline). Aliquots of these dilutions are placed in individual wells of Steer's Replicator and petri plates inoculated as previously described. The petri plates are incubated at 30° C. and read after 48 hours for yeast and 72 hours for fungi.

Table III lists the bacteria, yeast and fungi used in the MIC test described above along with their respective American Type Culture Collection (ATCC) identification numbers.

TABLE III

Organisms Used in the Minimum
Inhibitory Concentration Test

| Organism | ATCC No. |
|---|---|
| Bacteria | |
| Bacillus subtilis (Bs) | 8473 |
| Enterobacter aerogenes (Ea) | 13048 |
| Escherichia coli (Ec) | 11229 |
| Klebsiella pneumoniae (Kp) | 8308 |
| Proteus vulgaris (Pv) | 881 |
| Pseudomonas aeruginosa (Pa) | 10145 |
| Pseudomonas aeruginosa (PRD-10) | 15442 |
| Salmonella choleraesuis (Sc) | 10708 |
| Staphylococcus aureus (Sa) | 6538 |
| Yeast/Fungi | |
| Aspergillus niger (An) | 16404 |
| Candida albicans (Ca) | 10231 |
| Penicillium chrysogenum (Pc) | 9480 |
| Saccharomyces cerevisiae (Sc) | 4105 |
| Trichoderma viride (Tv) | 8678 |
| Aureobasidium pullulan (Ap) | 16622 |
| Fusarium oxysporum (Fo) | 48112 |

In Tables IV and V, the MIC values of the compounds described in Table II as compared to the MIC of a standard commercial preservative (with 1-(3-chloroallyl)-3,5,7-triaza-1-azoniaadamantane chloride as the active agent and referred to in Tables IV and V as "STANDARD I") are set forth for the bacteria organisms and yeast/fungi organisms which are listed in Table III.

TABLE IV

Minimum Inhibitory Concentrations for Test Compounds in Bacteria Species (in ppm)

| Compound | Bs | Ea | Ec | Kp | Pv | PRD | Pa | Sc | Sa |
|---|---|---|---|---|---|---|---|---|---|
| STANDARD | | | | | | | | | |
| pH 6.8 | 50 | 100 | 100 | 50 | 50 | 100 | 100 | 50 | 100 |
| pH 8.2 | 250 | 250 | 250 | 250 | 250 | 500 | >500 | 100 | 250 |
| (I) | | | | | | | | | |
| pH 6.8 | 100 | 100 | 100 | 100 | 100 | 100 | 100 | 100 | 100 |
| pH 8.2 | 500 | 501 | 501 | 501 | 500 | 501 | 501 | 501 | 501 |
| (II) | | | | | | | | | |
| pH 6.8 | 100 | 100 | 100 | 100 | 100 | 100 | 100 | 100 | 100 |
| pH 8.2 | 500 | 501 | 501 | 501 | 500 | 501 | 501 | 501 | 501 |

TABLE V

Minimum Inhibitory Concentrations for Test Compounds in Yeast/Fungi Species (in ppm)

| COMPOUND | An | Ca | Pc | Sc | Tv | Ap | Fo |
|---|---|---|---|---|---|---|---|
| STANDARD | >500 | >500 | >500 | 500 | >500 | >500 | >500 |
| I | 250 | 50 | 250 | 50 | 500 | 25 | 50 |
| II | 250 | 50 | 250 | 50 | 500 | 50 | 50 |

What is claimed is:

1. A process which comprises suspending from about 3 to about 70 weight percent of 2,2-dibromo-3-nitrilopropionamide in about 30 to about 97 weight percent water in the presence of a suspending amount of a thixotrope that exhibits Ellis-Plastic behavior at a pH of from about 1 to about 4.

2. The process according to claim 1 which comprises suspending from about 45 to about 55 weight percent of 2,2-dibromo-3-nitrilopropionamide in from about 45 to about 55 weight percent water.

3. The process according to claim 1 which comprises suspending from about 15 to about 25 weight percent of 2,2-dibromo-3-nitrilopropionamide in from about 75 to about 85 weight percent water.

4. The process of claim 1 in which the thixotrope is xantham gum, locust bean gum, or mixtures thereof.

5. The process of claim 1 in which the thixotrope is bentonite clay.

6. The process of claim 1 in which the suspending amount of the thixotrope is a mixture of from about 0.05 to about 1.5 weight percent xantham gum and from about 0.01 to about 0.5 weight percent locust bean gum.

7. The process of claim 1 which comprises adding an amount of acidifying agent to water which exhibits an initial basic pH to reduce the pH below about 7 before suspending the 2,2-dibromo-3-nitrilopropionamide.

8. An antimicrobial formulation which comprises from at least about 3 to at most about 70 weight percent 2,2-dibromo-3-nitrilopropionamide suspended in at least about 30 to at most about 97 weight percent water in the presence of a suspending amount of a thixotrope that exhibits Ellis-Plastic behavior at a pH of from about 1 to about 4.

9. The formulation according to claim 8 which comprises a suspension of from about 45 to about 55 weight percent 2,2-dibromo-3-nitrilopropionamide in from about 45 to about 55 weight percent water.

10. The formulation according to claim 8 which comprises a suspension of from about 15 to about 25 weight percent 2,2-dibromo-3-nitrilopropionamide in from about 75 to about 85 weight percent water.

11. The formulation of claim 8 in which the thixotrope is xantham gum, locust bean gum, or mixtures thereof.

12. The formulation of claim 8 in which the suspending amount of the thixotrope is a mixture of from about 0.05 to about 1.5 weight percent xantham gum and from about 0.01 to about 0.5 weight percent locust bean gum.

13. A method for biological control in an aqueous industrial system in need of such control which comprises contacting the system with an antimicrobially effective amount of the formulation of claim 8.

* * * * *